(12) United States Patent
Nagai et al.

(10) Patent No.: US 6,670,326 B1
(45) Date of Patent: Dec. 30, 2003

(54) DEPSIPEPTIDE COMPOUND

(75) Inventors: Koji Nagai, Tokyo (JP); Nakako Arao, Tokyo (JP); Kinya Souda, Ibaraki (JP); Kazuma Kamigiri, Tokyo (JP); Masamichi Mori, Ibaraki (JP); Nobuaki Shindo, Ibaraki (JP); Haruo Seto, Tokyo (JP); Kazuo Shin-Ya, Tokyo (JP)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/889,303

(22) PCT Filed: Jan. 12, 2000

(86) PCT No.: PCT/JP00/00110

§ 371 (c)(1), (2), (4) Date: Jul. 13, 2001

(87) PCT Pub. No.: WO00/42062

PCT Pub. Date: Jul. 20, 2000

(30) Foreign Application Priority Data

Jan. 13, 1999 (JP) .................................. 11-7040

(51) Int. Cl.⁷ .......... C07K 5/12; C07K 5/027; C07K 5/08; C07K 5/10; C12P 21/04

(52) U.S. Cl. .............. 514/10; 514/9; 514/18; 514/19; 530/317; 530/323; 530/330; 530/331; 530/344

(58) Field of Search ............... 514/10, 9, 18, 514/19; 530/317, 323, 330, 331, 344

(56) References Cited

FOREIGN PATENT DOCUMENTS

| EP | 0 352 646 | 1/1990 |
|---|---|---|
| JP | 61-101501 | 5/1986 |
| WO | 95/27730 | 10/1995 |

OTHER PUBLICATIONS

International Search Report.

*Primary Examiner*—Christopher S. F. Low
*Assistant Examiner*—Chih-Min Kam
(74) *Attorney, Agent, or Firm*—Sughrue Mion, PLLC

(57) ABSTRACT

This invention relates to a novel compound which has a cytotoxic activity and TGF-β like activity for human cancer cells and is useful as an antitumor agent and to a pharmaceutical composition which contains the same.

3 Claims, No Drawings

DEPSIPEPTIDE COMPOUND

This application is a 371 of PCT/JP00/00110, filed Jan. 12, 2000.

1. Technical Field

The present invention relates to a novel compound or a pharmaceutically acceptable salt thereof, which has a cytotoxic activity and TGF-β like activity for human cancer cells and is useful as medicaments, particularly as an antitumor agent, and to a pharmaceutical composition which contains said compound as the active ingredient.

2. Background Art

It is known that mitomycin C, bleomycin, adriamycin or the like compound derived from a microbial metabolite shows cytotoxic activity for human cancer cells, and these compounds are conventionally used as antitumor agents in the clinical field. Also, a depsipeptide compound is disclosed as an antitumor substance (European Patent Publication No. 352646).

Even at present, creation of antitumor agents having an unconventional chemical structure and novel skeleton is under examination.

On the other hand, TGF-β is first drawing attention as a factor which accelerates proliferation of cells and also accelerates transformation, it was now revealed that TGF-β acts as a factor which inhibits growth of various animal cells by the studies on its mechanism of actions (*Cell*, vol. 63, pp. 245–247, 1990). In addition, a large number of reports have been published regarding its relation to tumor cells (*Br. Med. J.*, vol. 296, pp. 1621–1624, 1988; *Br. J. Cancer*, vol. 61, pp. 612–617, 1990; *Br. J. Cancer*, vol. 69, pp. 1006–1009, 1994; *J. Cell Physiol.*, vol. 172, pp. 1–11, 1997; *Growth Factors*, vol. 7, pp. 207–213, 1992; *J. Biol. Chem.*, vol. 272, pp. 3967–3972, 1997; *Nature*, vol. 360, pp. 361–364, 1992). Also, it has been reported that TGF-β receptor acts as a tumor suppressor gene in various tumors (*International J. Hematology*, vol. 65, pp. 97–104, 1997). In consequence, a compound exhibiting TGF-β like activity has a possibility of becoming therapeutic agents for diseases related to said activity, such as an antitumor agent.

DISCLOSURE OF THE INVENTION

The invention aims at providing a novel compound which has a cytotoxic activity and TGF-β like activity for human cancer cells and is useful as an antitumor agent and a medicament which contains the same.

As a result of intensive studies on natural compounds produced by many microorganisms, the present inventors have found a microorganism, a microorganism of new species belonging to the genus Pseudomonas, which has the ability to produce a compound having excellent cytotoxic activity and TGF-β like activity for human cancer cells. Thereafter, the present inventors have cultured said microorganism and succeeded in isolating a novel depsipeptide compound from said culture mixture, which has a completely different structure from that of the aforementioned known depsipeptide compound (European Patent Publication No. 352646) in terms of the following chemical structure which has hydroxyl group at the 3-position, an R group (a group selected from any one of isopropyl group, sec-butyl group or isobutyl group) at the 4-position and methyl group at the 8-position, thereby accomplishing the invention.

Accordingly, the invention relates to (1) a depsipeptide compound represented by the following general formula

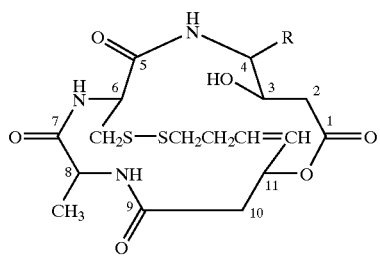

(wherein R represents isopropyl group, sec-butyl group or isobutyl group) or a pharmaceutically acceptable salt thereof. The invention also relates to a pharmaceutical composition which comprises the aforementioned depsipeptide compound or a pharmaceutically acceptable salt thereof as the active ingredient, preferably said pharmaceutical composition which is an antitumor agent.

The following describes the invention in detail. The depsipeptide compound of the invention or a pharmaceutically acceptable salt thereof can be obtained by culturing a said compound-producing bacterium belonging to the genus Pseudomonas in a nutrient medium and collecting accumulated said compound from the culture mixture in the usual way. Any microorganism can be used as the microorganism to be used in the production method of said compound, with the proviso that it is a microorganism which belongs to the genus Pseudomonas and has the ability to produce said compound. As such a microorganism, a bacterial strain Pseudomonas sp. Q71576 belonging to the genus Pseudomonas isolated from a soil sample collected at Mochizuki-cho, Kitasaku-gun, Nagano Prefecture, for example, can be cited. Bacterial properties of this strain are as follows.

1) Morphological Properties

This strain is a Gram-negative rod and has motility by polar flagella. Size of the cell is 0.7 to 0.9 μm×1.0 to 1.4 μm. Spore formation is not found.

2) Cultural Properties

It forms light brown colonies on a bouillon agar medium. The colony is circular and its surface is smooth. By a bouillon liquid culture, it formed pellicle on the medium surface and the entire medium was turbid. By a bouillon gelatin stab culture, it liquefied gelatin. By a litmus milk culture, coagulation and peptonization were not found after 1 week of the culturing.

3) Physiological Properties

TABLE 1

Physiological properties of strain Q71576 (1)

| | |
|---|---|
| Reduction of nitrate | negative |
| Denitrification reaction | negative |
| MR test | negative |
| VP test | negative |
| Formation of indole | negative |
| Formation of hydrogen sulfide | negative |
| Hydrolysis of starch | negative |
| Utilization of citric acid | positive |
| Utilization of nitrate | positive |
| Utilization of ammonium salt | positive |
| Formation of water-soluble fluorochrome | positive |
| Urease | negative |

TABLE 1-continued

Physiological properties of strain Q71576 (1)

| | |
|---|---|
| Oxidase | positive |
| Catalase | positive |
| Growth temperature range | 3 to 32° C. |
| Optimum growth temperature | 10 to 24° C. |
| Growth pH range | pH 5 to 9 |
| Optimum growth pH | pH 6 to 8 |
| Growth under anaerobic condition | negative |
| OF test | oxidation type |
| Arginine degradation reaction | positive |
| Growth in 3% NaCl-added bouillon medium | positive |

TABLE 2

Physiological properties of strain Q71576 (2)

Acid production from saccharides

| | |
|---|---|
| L-Arabinose | positive |
| D-Xylose | positive |
| D-Glucose | positive |
| D-Mannose | positive |
| D-Fructose | negative |
| Sucrose | negative |
| Inositol | negative |
| D-Mannitol | negative |
| D-Galactose | negative |
| Maltose | negative |
| Trehalose | negative |
| Lactose | negative |
| D-Sorbitol | negative |
| Glycerol | negative |
| Starch | negative |

TABLE 3

Physiological properties of strain Q71576 (3)

Assimilation of saccharides

| | |
|---|---|
| L-Arabinose | negative |
| D-Xylose | negative |
| D-Glucose | positive |
| D-Mannose | positive |
| D-Fructose | positive |
| Sucrose | negative |
| Inositol | positive |
| Rhamnose | negative |
| Raffinose | negative |
| D-Mannitol | positive |
| D-Galactose | positive |
| Maltose | negative |
| Trehalose | positive |
| Lactose | negative |
| D-Sorbitol | positive |
| Salicin | negative |
| Melibiose | negative |
| Glycerol | positive |
| Starch | negative |
| Xanthine | positive |
| Chitin | negative |

In summarizing the above microbiological properties, this strain is a Gram-negative aerobic rod and has motility. Its growth temperature range is from 3 to 32° C., its oxidase test, catalase test, gelatin liquefaction reaction, citric acid utilization, inorganic nitrogen source utilization and arginine degradation reaction are positive, it forms acid from L-arabinose, D-xylose, D-glucose and D-mannose and the result of the OF test is oxidation type. On the other hand, results of the formation of hydrogen sulfide, formation of indole, VP test, reduction of nitrate and denitrification reaction are negative.

When the aforementioned properties were referred to Bergey's Manual of Systematic Bacteriology (1989) and other literature, this strain was identified as a bacterium belonging to the genus Pseudomonas and named Pseudomonas sp. Q71576.

In this connection, this strain, named Pseudomonas sp. Q71576, has been internationally deposited as FERM BP-6944 (deposited on Jan. 8, 1999) in National Institute of Bioscience and Human Technology, Agency of Industrial Science and Technology (Higashi 1-1-3, Tsukuba-shi, Ibaraki Prefecture, Japan, the postal code 305-8566). Also, since microorganisms are apt to cause artificial or spontaneous mutation, the Pseudomonas sp. Q71576 includes not only microorganisms isolated from the nature but also those which are artificially mutagenized with ultraviolet rays, X rays, chemical drugs and the like and their spontaneous mutants.

(Production method)

The compound of the invention is obtained by culturing a microorganism which belongs to the genus Pseudomonas and has the ability to produce the compound of the invention. The culturing is carried out in accordance with a general microorganism culturing method.

The medium to be used in the culturing may be any medium which contains nutrient sources utilized by Pseudomonas sp. Q71576, and a synthetic medium, a semi-synthetic medium or a natural medium is used. Generally known materials can be used as the nutrients to be added to the medium. Regarding the medium composition, D-glucose, D-mannose, D-fructose, inositol, D-mannitol, D-galactose, trehalose, xanthine, starch, glucose, dextrin, glycerol, plant oil and the like can be cited as examples of the carbon source. As the nitrogen source, meat extract, peptone, gluten meal, cotton seed cake, soybean powder, peanut powder, fish meal, corn steep liquor, dry yeast, yeast extract, ammonium chloride, ammonium sulfate, ammonium nitrate, uric acid and other organic and inorganic nitrogen sources are used. Also, sulfate, nitrate, carbonate, phosphate and the like of sodium, potassium, magnesium, calcium, zinc, iron, cobalt and the like are added as metal salts as occasion demands. In addition, as occasion demands, methionine, cysteine, cystine, thiosulfate, methyl oleate, lard oil, silicon oil, surface active agent and the like formation accelerating compounds or antifoaming agents can also be added.

Regarding the culture conditions, culturing under an aerobic condition is generally advantageous, and the culturing is carried out at a temperature of from 3 to 32° C. (cf. the aforementioned description on the physiological properties), preferably from 20 to 25° C. Good results are obtained when the medium pH is adjusted to a range of approximately from 4.5 to 9, preferably from about 5 to 7.5. The culturing period is optionally decided in response to the medium composition and temperature condition, but is generally from about 1 to 7 days, preferably from about 2 to 4 days.

In order to isolate the compound of interest of the invention from the culture mixture, techniques usually used for the extraction and purification of metabolites produced by microorganisms can be optionally employed. For example, said compound among compounds in the culture mixture is extracted by adding ethyl acetate or the like organic solvent which does not mix with water directly to the culture broth or to a culture filtrate obtained by centrifugation or by filtration after adding a filter aid to the culture mixture. Said compound can also be extracted by allowing the culture broth to contact with an appropriate carrier, thereby effecting adsorption of the produced compound in the culture broth to the carrier, and then eluting the compound with an appropriate solvent. For example, said compound is adsorbed by allowing it to contact with a porous adsorption resin such as Amberlite XAD-2, Diaion HP-20, Diaion CHP-20 or Diaion SP-900. Next, said compound is eluted using an organic solvent such as methanol, ethanol, acetone, butanol, acetonitrile or chloroform, alone or as a mixture, or a mixed solution of said solvent with water. In the latter case, a fraction containing more higher ratio of said compound can be obtained by increasing mixing ratio of the organic solvent from a low concentration to a high concentration stepwise or continuously. When extracted with ethyl acetate, chloroform and the like organic solvents, said compound is extracted by adding these solvents to the culture filtrate and thoroughly shaking the mixture. Thereafter, said compound contained in the fraction thus obtained using the above each technique can be separated and purified with more higher purity by employing a usually used method such as a column chromatography which uses silica gel, ODS or the like, a centrifugal liquid-liquid partition chromatography or a high performance liquid chromatography (HPLC) which uses ODS.

On the other hand, it can also be separated and purified using the TGF-β like activity as the marker, by certain means which are used in the production of general physiologically active compounds making use, for example, of the difference in its solubilizing ability or solubility in appropriate solvents. As occasion demands, these methods can be used alone or repeatedly by combining them in an optional order.

The pharmaceutically acceptable salt of the depsipeptide compound of the invention is a salt with an inorganic or organic base, and a pharmaceutically acceptable salt is desirable. Illustrative examples of these salts include salts with inorganic bases such as sodium, potassium, magnesium, calcium and aluminum, organic bases such as methylamine, ethylamine and ethanolamine, and basic amino acids such as lysine and ornithine.

Also, since the compound of the invention has asymmetric carbon atoms and double bonds, stereoisomers (racemic bodies, optical isomers, diastereomers and the like) and geometrical isomers (cis-forms or trans-forms) are present based on this. Consequently, mixtures or isolated products of these stereoisomers or geometrical isomers are included in the compound of the invention.

In addition, hydrates or various solvates of said compound and polymorphism of said compound are also included in the invention.

The formulation method and administration method of the compound of the invention are described in detail in the following.

The pharmaceutical composition which contains one or two or more of the depsipeptide compounds of the invention or pharmaceutically acceptable salts thereof as the active ingredient is prepared into tablets, powders, fine subtilaes, granules, capsules, pills, solutions, injections, suppositories, ointments, adhesive preparations and the like using generally used pharmaceutical carriers, fillers and other additives and administered orally or parenterally.

Clinical dose of the compound of the invention in human is optionally decided by taking into consideration symptoms, weight, age, sex and the like of each patient to be treated.

The solid composition for use in the oral administration according to the invention is used in the form of tablets, powders, granules and the like. In such a solid composition, one or more active compounds are mixed with at least one inert diluent such as lactose, mannitol, glucose, hydroxypropylcellulose, microcrystalline cellulose, starch, polyvinyl pyrrolidone or aluminum magnesium silicate. In accordance with the usual way, the composition may contain other additives than the inert diluent, such as magnesium stearate or the like lubricant, calcium cellulose glycolate or the like disintegrating agent, lactose or the like stabilizing agent and a solubilization assisting agent. If necessary, tablets or pills may be coated with a sugar such as sucrose, gelatin, hydroxypropylcellulose, hydroxypropylmethylcellulose phthalate or the like or with a film of a gastric or enteric compound.

The liquid composition for oral administration includes pharmaceutically acceptable emulsions, solutions, suspensions, syrups, elixirs and the like and contains a generally used inert diluent such as purified water or ethyl alcohol. In addition to the inert diluent, this composition may also contain a solubilization assisting agent, a moistening agent, a suspending agent and the like auxiliary agents, as well as sweeteners, flavors, aromatics and antiseptics.

The injections for parenteral administration include aseptic aqueous or non-aqueous solutions, suspensions and emulsions. Examples of the diluent for use in the aqueous solutions and suspensions include distilled water for injection use and physiological saline. Examples of the diluent for use in the non-aqueous solutions and suspensions include propylene glycol, polyethylene glycol, olive oil or the like plant oil, ethyl alcohol or the like alcohol, polysorbate 80 (trade name) and the like. Such a composition may further contain additive agents such as a tonicity agent, an antiseptic, a moistening agent, an emulsifying agent, a dispersing agent, a stabilizing agent (e.g., lactose) and a solubilization assisting agent. These compositions are sterilized by filtration through a bacteria retaining filter, blending of a germicide or irradiation. Alternatively, they may be used by firstly making into sterile solid compositions and then dissolving them in sterile water or a sterile solvent for injection use prior to their use.

If solubility of the compound of the invention is low, its solubilization treatment may be carried out. The solubilization treatment can be effected by a known method which can be applied to pharmaceutical preparations, such as a method in which surface active agents (polyoxyethylene hydrogenated castor oil, polyoxyethylene sorbitan higher fatty acid esters, polyoxyethylene polyoxypropylene glycols, sucrose fatty acid esters and the like) are added or a method in which a solid dispersion of the drug is formed with a solubilizing agent such as a polymer (hydroxypropylmethylcellulose (HPMC), polyvinyl pyrrolidone (PVP), polyethylene glycol (PEG) or the like water-soluble polymer or carboxymethylethylcellulose (CMEC), hydroxypropylmethylcellulose phthalate (HPMCP), a methyl methacrylate-methacrylic acid copolymer (Eudragit L, S, trade name; mfd. by Rohm & Haas) or the like enteric polymer). If necessary, a method to form a soluble salt or a method to form an inclusion compound using cyclodextrin or the like can also be employed. The means for effecting solubilization can be optionally changed in response to the drug of interest [cf., "Recent Formulation Techniques and their Application I", I. Utsumi et al., Medical Journal 157–159 (1983) and "Pharmacy Monograph No. 1, Bioavailability", K. Nagai et al., Soft Science, 78–82 (1988)].

BEST MODE FOR CARRYING OUT THE INVENTION

The following describes the invention illustratively with reference to examples, but the invention is not limited to them.

EXAMPLE 1

A medium containing 10 g of glucose, 20 g of potato starch, 5 g of polypeptone, 5 g of yeast extract, 4 g of calcium carbonate and 1 liter of distilled water (pH 7.0) was dispensed in 100 ml portions into 500 ml Erlenmeyer flasks and sterilized at 120° C. for 20 minutes. Cells of Pseudomonas sp. Q71576 well grown on Bennett agar medium were scratched off, inoculated into the medium and cultured at 28° C. for 3 days on a shaker under a condition of 200 rotation/min to be used as the seed culture broth. Next, a medium containing 30 g of glycerol, 1 g of glucose, 5 g of polypeptone, 5 g of meat extract, 5 g of NaCl, 0.5 g of an antifoaming agent (NKL 5430) and 1 liter of distilled water (pH 7.0) was dispensed in 100 ml portions into 500 ml Erlenmeyer flasks and sterilized at 120° C. for 20 minutes. The aforementioned seed culture broth was inoculated in 2 ml portions into this medium and cultured at 28° C. for 3 days on a shaker under a condition of 200 rotation/min.

A 2.5 liter portion of the thus cultured broth was centrifuged at 6,000 rpm for 10 minutes. The supernatant was extracted with ethyl acetate, dehydrated by adding sodium sulfate and then concentrated to dryness under a reduced pressure. The oily crude extract was applied to a silica gel column chromatography (30 i.d.×200 mm), washed with chloroform-methanol (20:1) and then eluted with chloroform-methanol (5:1), and the active fraction was concentrated. Next, this was applied to a Sephadex LH-20 column chromatography (20 i.d.×500 mm) to carry out gel filtration with chloroform-methanol (1:1). The active fraction was concentrated and then applied to a CPC (centrifugal partition chromatography), and impurities were removed with a chloroform-methanol-water (5:6:4) solvent system using an ascending method. After finally concentrating the active fraction to dryness, this was dissolved in methanol to carry out a reverse phase HPLC (flow rate, 10 ml/min) with 35% acetonitrile aqueous solution using a PEGASIL ODS column (20 i.d.×250 mm) manufactured by Senshu Scientific. As a result, peak of the compound A was observed at 10.8 minutes, and that of the compound B at 15.4 minutes, and 10 mg of white powder of each of the compounds A and B was obtained by fractionating respective peaks.

EXAMPLE 2

A medium containing 10 g of glucose, 20 g of potato starch, 5 g of polypeptone, 5 g of yeast extract, 4 g of calcium carbonate and 1 liter of distilled water (pH 7.0) was dispensed in 100 ml portions into 500 ml Erlenmeyer flasks and sterilized at 120° C. for 20 minutes. Cells of Pseudomonas sp. Q71576 well grown on Bennett agar medium were scratched off, inoculated into the medium and cultured at 28° C. for 3 days on a shaker under a condition of 200 rotation/min. The same medium was dispensed in 400 ml portions into 2 liter Erlenmeyer flasks and sterilized at 120° C. for 20 minutes, and then 8 ml of the aforementioned seed culture broth was inoculated into this medium and cultured at 28° C. for 3 days on a shaker under a condition of 200 rotation/min to be used as the seed culture broth. Next, a medium containing 30 g of mannitol, 5 g of polypeptone, 5 g of meat extract, 5 g of sodium chloride and 1 liter of tap water (pH 7.0) was dispensed in 18 liter portions into three 30 liter capacity jar fermentors and sterilized at 120° C. for 20 minutes. The above seed culture broth was inoculated in 360 ml portions into this medium and cultured at 24° C. for 64 hours under conditions of 150 rotation/min and 1 vvm.

A 50 liter portion of the culture broth separated from the cells by Sharples was applied to a column packed with HP-20, washed with water, 20% acetone aqueous solution and 40% methanol aqueous solution and then eluted with 80% acetone aqueous solution. An aqueous solution obtained by concentrating the eluted fraction was extracted with chloroform and ethyl acetate, and the extracts were combined, concentrated and then applied to a column packed with silica gel. This was eluted with chloroform-methanol (50:1), (20:1) and (10:1), and predetermined portions of the chloroform-methanol (20:1) and (10:1) elution fractions were combined, concentrated and then dissolved in ethanol to carry out recrystallization, thereby obtaining 776 mg of white powder as a mixture containing the compounds A, B and C. By carrying out fractionation of the compound C elution fraction from the thus obtained powder using an ODS-HPLC column (cosmosil AR-II, 20 i.d.×250 mm), 20 mg of the compound C was obtained as white powder. Physicochemical properties of the compounds of the invention The compounds A, B and C which have been extracted, purified and isolated by the above techniques showed the following physicochemical properties.

TABLE 4

Physicochemical properties of compounds A, B and C

| | Compound A | Compound B | Compound C |
|---|---|---|---|
| Color and shape | White powder | White powder | White powder |
| Melting point | 135–138° C. | 132–135° C. | N.T. |
| Angle of rotation $[\alpha]_D^{25}$ | −63.6° (c 0.14, MeOH) | −58.6° (c 0.11, MeOH) | −60.0° (c 0.10, MeOH) |
| Molecular formula | $C_{20}H_{31}N_3O_6S_2$ | $C_{21}H_{33}N_3O_6S_2$ | $C_{21}H_{33}N_3O_6S_2$ |
| High resolution FAB mass spectrum Found Calcd | 474.1735 (M + H)+ 474.1733 | 488.1865 (M + H)+ 488.1889 | 488.1889 (M + H)+ 488.1889 |
| UV and visible region absorption spectrum $\lambda_{max}^{MeOH}$ nm (ε) | End absorption | End absorption | End absorption |
| IR absorption spectrum $\nu_{max}$ cm$^{-1}$ | 3400, 3350, 1720, 1660, 1520, 1260, 980 (KBr method) | 3400, 3350, 1720, 1660, 1520, 1260, 980 (KBr method) | 3400, 3320, 1730, 1660, 1550, 1280, 980 (reflectance method) |

N.T.: not tested

The $^1$H and $^{13}$C NMR chemical shift values (in CDCl$_3$) of compounds A, B and C are respectively shown below.

TABLE 5

The $^1$H and $^{13}$C NMR chemical shift values (in CDCl$_3$) of compound A

| No. | $\delta_c$ | $\delta_H$ |
|---|---|---|
| 1 | 171.3 | |
| 2 | 52.2 | 4.21 (dq, J = 4.0, 7.5 Hz) |
| 3 | 16.5 | 1.48 (d, J = 7.5 Hz) |
| NH | | 6.28 (m) |

TABLE 5-continued

The $^1$H and $^{13}$C NMR chemical shift values (in $CDCl_3$) of compound A

| No. | $\delta_c$ | $\delta_H$ |
|---|---|---|
| 1' | 169.1 | |
| 2' | 54.9 | 4.84 (dt, J = 3.5, 9.0 Hz) |
| 3' | 40.9 | 3.13 (m), 3.28 (m) |
| NH | | 6.79 (d, J = 9.0 Hz) |
| 1" | 171.7 | |
| 2" | 39.5 | 2.68 (d, J = 4.0 Hz) |
| 3" | 69.1 | 4.52 (m) |
| 4" | 63.4 | 2.77 (m) |
| 5" | 29.7 | 2.34 (m) |
| 6" | 19.7 | 0.90 (d, J = 7.0 Hz) |
| 7" | 20.6 | 1.00 (d, J = 7.0 Hz) |
| NH | | 7.38 (d, J = 7.0 Hz) |
| OH | | 3.09 (d, J = 10.0 Hz) |
| 1''' | 170.8 | |
| 2''' | 40.3 | 2.59 (d, J = 13.0 Hz), 3.31 (dd, J = 7.0, 13.0 Hz) |
| 3''' | 70.7 | 5.48 (m) |
| 4''' | 128.9 | 5.68 (d, J = 15.0 Hz) |
| 5''' | 133.3 | 6.31 (m) |
| 6''' | 33.1 | 2.43 (m), 2.68 (m) |
| 7''' | 40.9 | 2.73 (m), 3.24 (m) |

The number (No.) in the table indicates respective positions of carbon atoms in the chemical structural formula of compound A shown in the following.

TABLE 6

The $^1$H and $^{13}$C NMR chemical shift values (in $CDCl_3$) of compound B

| No. | $\delta_c$ | $\delta_H$ |
|---|---|---|
| 1 | 171.2 | |
| 2 | 52.2 | 4.22 (dq, J = 4.0, 7.0 Hz) |
| 3 | 16.6 | 1.48 (d, J = 7.0 Hz) |
| NH | | 6.18 (m) |
| 1' | 169.2 | |
| 2' | 54.5 | 4.87 (dt, J = 3.0, 9.0 Hz) |
| 3' | 41.3 | 3.10 (m), 3.33 (m) |
| NH | | 6.75 (d, J = 9.0 Hz) |
| 1" | 171.8 | |
| 2" | 39.5 | 2.70 (d, J = 4.0 Hz) |
| 3" | 68.2 | 4.60 (m) |
| 4" | 61.7 | 2.94 (m) |
| 5" | 36.3 | 2.05 (m) |
| 6" | 27.1 | 1.21 (m), 1.53 (m) |
| 7" | 11.5 | 0.89 (t, J = 7.5 Hz) |
| 8" | 15.4 | 0.90 (d, J = 7.0 Hz) |
| NH | | 7.25 (d, J = 7.0 Hz) |
| OH | | 2.93 (m) |
| 1''' | 170.6 | |
| 2''' | 40.7 | 2.58 (d, J = 13.0 Hz), 3.31 (dd, J = 7.0, 13.0 Hz) |
| 3''' | 70.6 | 5.48 (m) |
| 4''' | 128.6 | 5.67 (d, J = 15.0 Hz) |
| 5''' | 133.4 | 6.36 (m) |
| 6''' | 33.3 | 2.44 (m), 2.71 (m) |
| 7''' | 40.5 | 2.72 (m), 3.20 (m) |

The number (No.) in the table indicates respective positions of carbon atoms in the chemical structural formula of compound B shown in the following.

TABLE 7

The $^1$H and $^{13}$C NMR chemical shift values (in $CDCl_3$) of compound C

| No. | $\delta_c$ | $\delta_H$ |
|---|---|---|
| 1 | 171.3 | |
| 2 | 52.3 | 4.22 (dq, J = 7.3, 3.7 Hz) |
| 3 | 16.5 | 1.50 (d, J = 7.3 Hz) |
| NH | | 6.40 (br) |
| 1' | 168.9 | |
| 2' | 55.1 | 4.81 (m) |
| 3' | 41.1 | 3.20 (m) |
| NH | | 6.82 (d, J = 9.1 Hz) |
| 1" | 171.4 | |
| 2" | 38.8 | 2.68 (m) |
| 3" | 70.7 | 4.35 (m) |
| 4" | 56.0 | 3.08 (m) |
| 5" | 38.8 | 1.51 (m), 2.06 (m) |
| 6" | 25.2 | 1.62 (m) |
| 7" | 21.3 | 0.91 (d, J = 6.7 Hz) |
| 8" | 23.4 | 0.91 (d, J = 6.7 Hz) |
| NH | | 7.49 (d, J = 6.7 Hz) |
| OH | | 2.96 (br) |
| 1''' | 170.9 | |
| 2''' | 40.3 | 2.62 (d, J = 12.8 Hz), 3.36 (d, J = 12.8, 7.3 Hz) |
| 3''' | 70.7 | 5.48 (m) |
| 4''' | 129.0 | 5.72 (d, J = 15.8 Hz) |
| 5''' | 133.2 | 6.29 (m) |
| 6''' | 32.7 | 2.43 (m), 2.72 (m) |
| 7''' | 40.5 | 2.74 (m), 3.31 (m) |

The number (No.) in the table indicates respective positions of carbon atoms in the chemical structural formula of compound C shown in the following.

Based on the above physicochemical properties, chemical structural formulae of the compounds A, B and C were determined as follows.

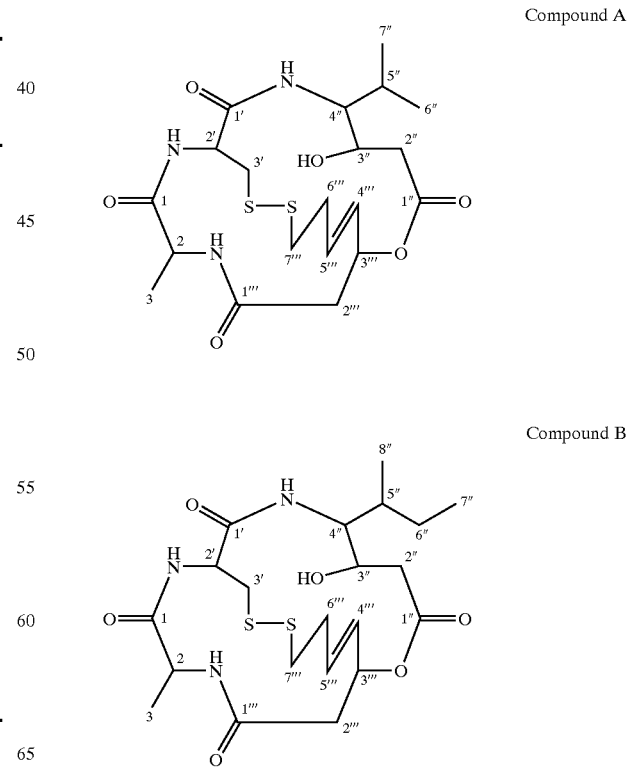

Compound A

Compound B

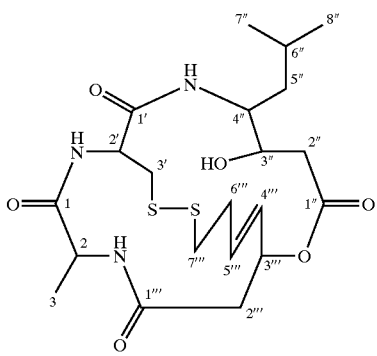

Compound C

Industrial Applicability

Since the compound of the invention has a cytotoxic activity and TGF-β like activities for human cancer cells, it is useful as an antitumor agent, for example as a drug or the like for colorectal cancer, lung cancer, prostatic cancer, cervical cancer or the like.

The cytotoxic activity and TGF-β like activity of the compound of the invention for human cancer cells were confirmed by the following methods.

Measurements of Cytotoxic Activity for Human Cancer Cells (1)

HeLa S3 cells adjusted to a density of $6 \times 10^4$ cells/ml were dispensed in 200 μl portions, and variations concentrations of the compound A and compound B respectively in 4 μl portions, into a 96 well test plate, and cultured at 37° C. for 3 days in a $CO_2$ incubator. After the culturing, the degree of cell growth was measured using Cell Counting Kit (mfd. by DOJINDO), and the growth inhibition ration at each concentration was obtained to calculate the $IC_{50}$ value. As a result, the compound A and compound B showed cytotoxic activity for HeLa S3 cells with the $IC_{50}$ values of 1.6 μM and 1.2 μM, respectively.

Measurement of Cytotoxic Activity for Human Cancer Cells (2)

Human colon cancer WiDr cells adjusted to a density of $6 \times 10^4$ cells/ml, human non-small cell lung carcinoma A549 cells adjusted to a density of $4 \times 10^4$ cells/ml or $6 \times 10^4$ cells/ml were dispensed into a 96 well test plate and cultured at 37° C. in a $CO_2$ incubator. After 24 hours varied concentration of the compound A, compound B or compound C was dispensed in 100 μl portions, and the cells were cultured at 37° C. for additional 72 hours in a $CO_2$ incubator. After the culturing, the number of cells was determined using Sulforhodamine B, and the $IC_{50}$ value of each compound for cell growth was calculated. As a result, the compounds A, B and C showed excellent cell growth inhibition activity for respective cell species WiDr cells, A549 cells or DU-145 cells. Though it varies depending on the cell species, for example for A549 cells, the compounds showed the activity with an $IC_{50}$ value of 5.0 nM or less.

Measurement of TGF-β Like Activity

In order to detect the TGF-β like activity, a screening system was constructed making use of the expression of a reporter gene. A luciferase gene was transfected into downstream of the PAI-1 promoter gene of mink lung epithelial cells (Mv1Lu) in which expression of plasminogen activator-1 (PAI-1) is induced by TGF-β due to excess expression of TGF-β receptor (*Journal of Biological Chemistry*, vol. 262, pp. 17467–17474, 1987), (*Analytical Biochemistry*, vol. 216, pp. 276–284, 1994).

Using the above cells, the luminous intensity obtained by adding each compound was used as the index of TGF-β like activity. As a result, TGF-β increased the luminous intensity induced by the expression of PAI-1 promoter gene. In the same manner, compound A increased the luminous intensity at a concentration of from 26 nM to 100 μM, and compound B at a concentration of from 12 nM to 100 μM.

What is claimed is:

1. An isolated depsipeptide compound represented by the following formula

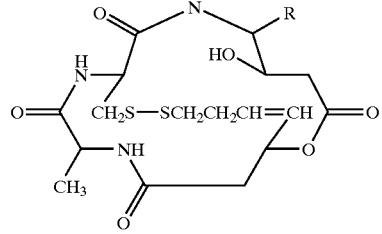

or a pharmaceutically acceptable salt thereof, wherein R is isopropyl, sec-butyl or isobutyl group.

2. A pharmaceutical composition which comprises the depsipeptide compound or a pharmaceutically acceptable salt thereof described in claim 1 as the active ingredient.

3. The pharmaceutical composition according to claim 2, wherein the active ingredient is an antitumor agent.

* * * * *